US009241634B2

(12) United States Patent
Wang et al.

(10) Patent No.: US 9,241,634 B2
(45) Date of Patent: Jan. 26, 2016

(54) ANALYTIC MORPHOMICS: HIGH SPEED MEDICAL IMAGE AUTOMATED ANALYSIS METHOD

(71) Applicant: The Regents of The University of Michigan, Ann Arbor, MI (US)

(72) Inventors: Stewart Wang, Ann Arbor, MI (US); Sven Alan Holcombe, Ann Arbor, MI (US); Hannu Huhdanpaa, Brighton, MI (US); June Sullivan, Ann Arbor, MI (US); Carla Kohoyda-Inglis, Grass Lake, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 197 days.

(21) Appl. No.: 14/014,485

(22) Filed: Aug. 30, 2013

(65) Prior Publication Data
US 2014/0064583 A1    Mar. 6, 2014

Related U.S. Application Data

(60) Provisional application No. 61/694,944, filed on Aug. 30, 2012.

(51) Int. Cl.
*A61B 5/00* (2006.01)
*A61B 6/03* (2006.01)
(Continued)

(52) U.S. Cl.
CPC ............. *A61B 5/004* (2013.01); *A61B 6/032* (2013.01); *A61B 6/463* (2013.01); *A61B 6/505* (2013.01);
(Continued)

(58) Field of Classification Search
None
See application file for complete search history.

(56) References Cited

U.S. PATENT DOCUMENTS 5,509,042 A * 4/1996 Mazess ........................... 378/54
5,850,836 A * 12/1998 Steiger et al. ................. 600/300
(Continued)

FOREIGN PATENT DOCUMENTS

| EP | 0501993 | 9/1992 |
| JP | 2012034988 | 2/2012 |

(Continued)

OTHER PUBLICATIONS

Lin et al. "Computer-Aided Kidney Segmentation on Abdominal CT images," published in 2006.*
(Continued)

*Primary Examiner* — Vu Le
*Assistant Examiner* — Alexander J Lesnick
(74) *Attorney, Agent, or Firm* — Harness, Dickey & Pierce, PLC

(57) ABSTRACT

A computer-implemented method is provided for anatomically indexing a subject. The method includes: receiving image scan data representing a volume of a subject, where the image scan data is comprised of a plurality of image slices of the subject and includes at least a portion of a vertebral column of the subject; identifying the vertebral canal of the vertebral column of the subject in the image scan data; determining a plurality of markers for the vertebral column, where each marker is indicative of a different vertebral body of the vertebral column and includes its location in the image scan data defined in a coordinate system, such that the plurality of markers define a vertebral level coordinate system; and storing each marker along with its location in a database. The markers can subsequently be used to reference other anatomical components of the subject across different image scans.

19 Claims, 7 Drawing Sheets

(51) Int. Cl.
 *A61B 6/00* (2006.01)
 *G06T 7/00* (2006.01)
 *G01R 33/56* (2006.01)

(52) U.S. Cl.
 CPC ............ *A61B 6/5217* (2013.01); *G06T 7/0081* (2013.01); *G06T 7/0097* (2013.01); *G01R 33/5608* (2013.01); *G06T 2200/04* (2013.01); *G06T 2207/10081* (2013.01); *G06T 2207/30012* (2013.01)

(56) References Cited

U.S. PATENT DOCUMENTS

| | | | |
|---|---|---|---|
| 7,899,225 B2 | 3/2011 | Collins et al. | |
| 7,916,917 B2 * | 3/2011 | Dewaele et al. | 382/128 |
| 7,949,167 B2 | 5/2011 | Krishnan et al. | |
| 2007/0030346 A1 * | 2/2007 | Feuerlein | 348/77 |
| 2009/0142740 A1 * | 6/2009 | Liang et al. | 434/262 |
| 2009/0202122 A1 * | 8/2009 | Wang | 382/128 |
| 2010/0329529 A1 | 12/2010 | Feldman et al. | |
| 2011/0021914 A1 * | 1/2011 | Zheng et al. | 600/443 |
| 2011/0142320 A1 * | 6/2011 | Gupta et al. | 382/131 |
| 2011/0150176 A1 | 6/2011 | Koehler et al. | |
| 2011/0166879 A1 | 7/2011 | Lee et al. | |
| 2011/0228995 A1 * | 9/2011 | Batman et al. | 382/128 |
| 2011/0286630 A1 * | 11/2011 | Harder et al. | 382/103 |
| 2012/0143090 A1 * | 6/2012 | Hay et al. | 600/587 |

FOREIGN PATENT DOCUMENTS

| | | |
|---|---|---|
| WO | WO2011092531 | 8/2011 |
| WO | WO 2011092531 A1 * | 8/2011 |

OTHER PUBLICATIONS

Englesbe, et al "Analytic Morphomics, Core Muscle Size and Surgical Outcomes", Ann Surg. (2011).

* cited by examiner

![US 9,241,634 B2]

ANALYTIC MORPHOMICS: HIGH SPEED MEDICAL IMAGE AUTOMATED ANALYSIS METHOD

CROSS-REFERENCE TO RELATED APPLICATIONS

This application claims the benefit of U.S. Provisional Application No. 61/694,944 filed on Aug. 30, 2012. The entire disclosure of the above application is incorporated herein by reference.

FIELD

The present disclosure relates to systems and methods for facilitating high speed medical image analysis.

BACKGROUND

In medical research fields, obtaining uniform image scans, e.g., computed tomography (CT) scans, for medical research or treatment (evaluation) is difficult. In particular, because of the radiation the subjects of the image scan are exposed to, image scans are typically only performed when there is a medical need for the image scan. Furthermore, the image scans may be ordered to only capture relevant portions of the subject's body. The result is a non-ideal distribution of image scans from a medical research or treatment (evaluation) perspective. As can be appreciated, subjects come in varying shapes and sizes. Thus, image scans can vary in the amount of a subject that is depicted in the image scan. Furthermore, as the image scans are performed on a medical need basis, the focus of the image scans varies. For instance, if a physician orders a scan of a subject's neck area, then the entire cervical vertebral column may be included in the image scan, but only a small portion of the skull base and upper thoracic vertebrae. If, however, the physician orders a scan of the subject's lower-abdominal area, the upper-portion of the subject's image scan may not be included in the image scan. Accordingly, for purposes of computer-aided analysis of image scans, it can be difficult to analyze image scans corresponding to many different patients due to the lack of uniformity in the collection of image scans.

This section provides background information related to the present disclosure which is not necessarily prior art.

SUMMARY

This section provides a general summary of the disclosure, and is not a comprehensive disclosure of its full scope or all of its features.

A computer-implemented method is provided for anatomically indexing a subject. The method includes: receiving image scan data representing a volume of a subject, where the image scan data is comprised of a plurality of image slices of the subject and includes at least a portion of a vertebral column of the subject; identifying the vertebral canal of the vertebral column of the subject in the image scan data; determining, by the image processor, a plurality of markers for the vertebral column, each marker is indicative of a different vertebral body of the vertebral column and includes its location in the image scan data defined in a coordinate system, such that the plurality of markers define a vertebral level coordinate system; and storing each marker along with its location in a database.

In another aspect of this disclosure, the method for anatomically indexing begins by retrieving a plurality of markers for a vertebral column from a database, where each marker is indicative of a different vertebral body of the vertebral column and includes its location in the image scan data defined in a coordinate system, such that the plurality of markers define a vertebral level coordinate system. The method further includes determining location of an anatomical component of the subject from image scan data representing a volume of the subject; determining a measure for the anatomical component; associating the measure for the anatomical component with the location of the anatomical component, such that the location of the anatomical component expressed in the vertebral level coordinate system; and storing the measure for the anatomical component along with the location of the anatomical component in a database.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Image scans that are used for medical research have a low degree of uniformity. As used herein, the term image scan may refer to computer tomography (CT) scans or other x-ray scans. The term "image scan" may further refer to other types of images, such as magnetic resonance images (MRIs). Because of the low degree of uniformity, techniques are disclosed herein for indexing individual image scans to locate one or more markers within the scan. The markers are used to collectively define one or more body coordinate systems. The body coordinate systems can be applied across a collection of image scans. Furthermore, when medical research is performed on the collection of image scans, measurements can be taken using the one or more body coordinate systems.

Figure 1:
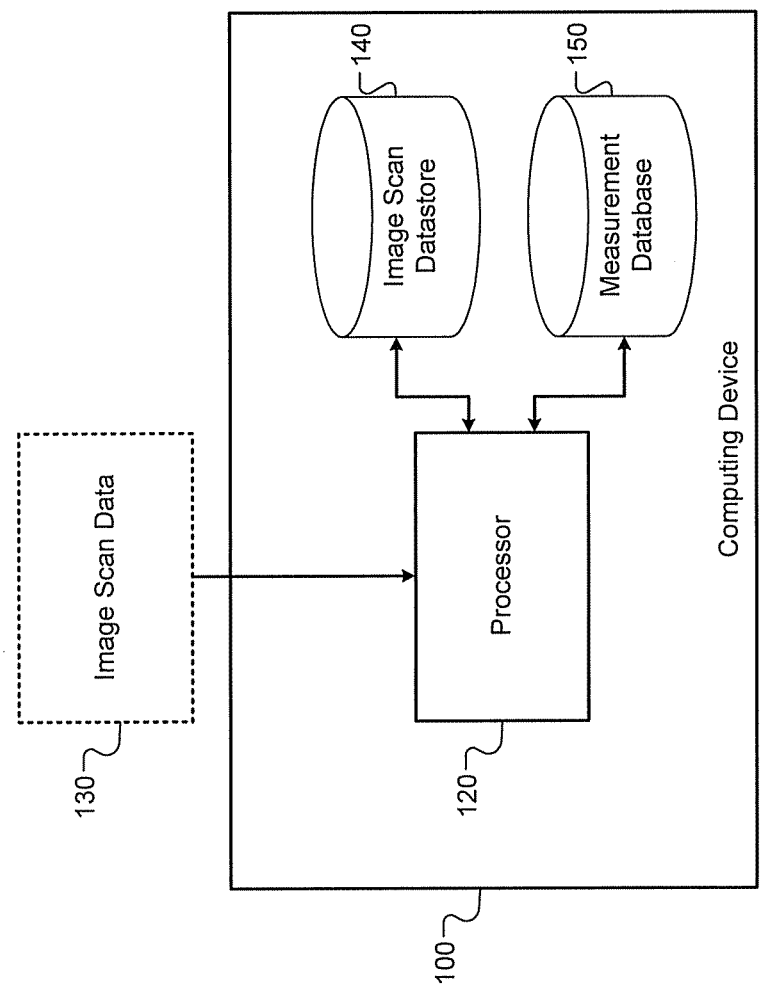
FIG. 1 is a component block diagram illustrating an exemplary computing device configured to analyze and index an image scan according to some embodiments of the present disclosure.

Referring now to FIG. 1, an example computing device 100 is depicted. The computing device 100 includes a processor 120 that analyzes and indexes image scan data 130, an image scan datastore 140, and a measurements database 150. It should be appreciated that the computing device 100 can include additional components that are not shown. The system may further include an image device, such as a tomograph, which can be used to capture image scan data representing a volume of the subject.

The processor 120 is configured to receive image scan data from one or more sources. While one processor 120 is depicted, the term "processor" can include two or more processors operating in an parallel or distributed manner. The image scan data can include an image scan and metadata corresponding to the image scan. The image scan represents a volume of a subject and can be comprised of a plurality of image slices that collectively define a volume of the subject.

Figure 2:
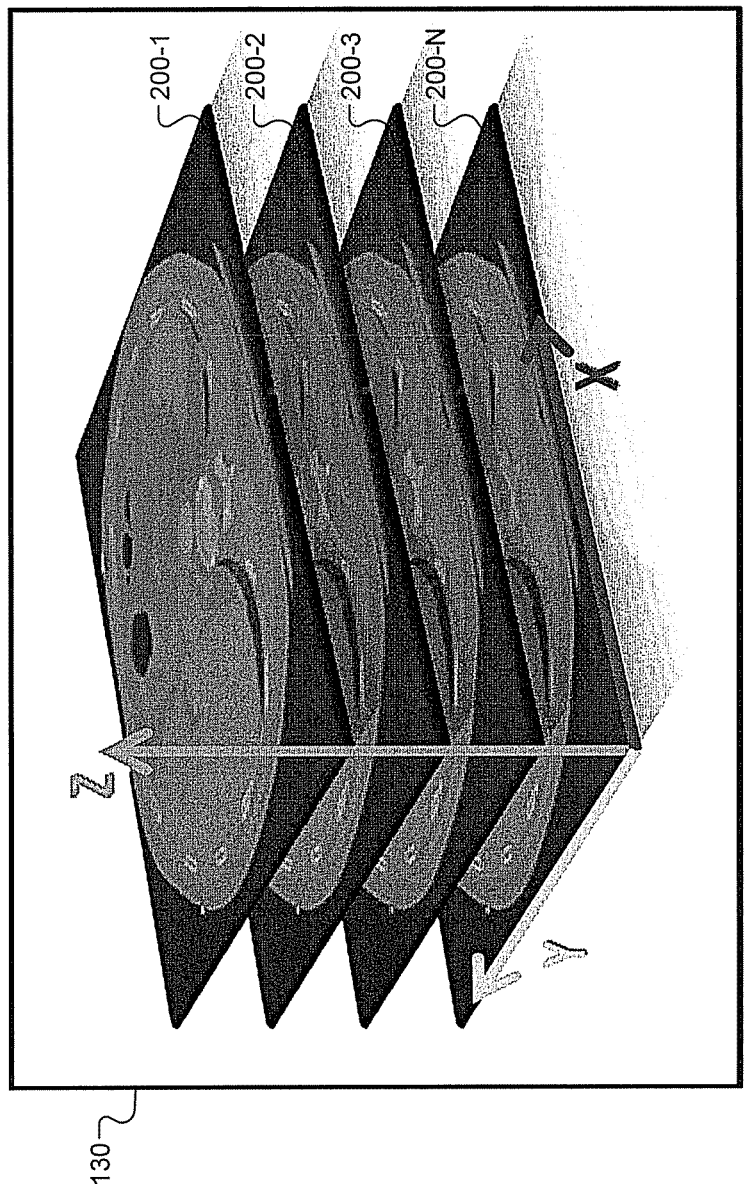
FIG. 2 is a schematic illustrating an example of an image scan comprised of a plurality of image slices.

FIG. 2 illustrates an exploded view of an example image scan 130. In FIG. 2, the image scan 130 is comprised of N image scan slices, e.g., image slice 200-1, image slice 200-2, image slice 200-3 ... image slice 200-N (individually referred to as image slice 200). In some embodiments, the image scan 130 can be defined in a three dimensional space, such that any point in the image scan 130 can be referenced by an (x, y, z) coordinate. In the illustrated example, the z-coordinate can represent a particular image slice 200, and the (x, y) coordinates can represent a particular point in the particular image slice 200. In some embodiments, the (x, y) coordinates refer to individual pixels in the image scan 130. While the illustrated example references an image slice 200 by the z-coordinate, it should be appreciated that an image slice 200 can be referenced by the x-coordinate or the y-coordinate. Furthermore, while a Cartesian coordinate system is described, it should be appreciated that other coordinate systems, such as polar coordinate systems may be used to reference points within an image scan.

Referring back to FIG. 1, the metadata of the image scan data can include an image scan identifier. The image scan identifier can be, for example, a number or an alphanumeric string that uniquely identifies the image scan from other image scans. It should be appreciated that the metadata can include other types of data as well. For example, the metadata can further include an age of the subject depicted in the image scan.

The processor 120 is further configured to analyze the image scan to locate one or more markers within the image scan 130. A marker can be any predetermined component within the image scan. The processor 120 can locate one or more particular points and/or shapes of the predetermined component, such that the marker in the image scan 130 can be identified by the one or more particular points and/or shapes. In some embodiments, the markers correspond to vertebral bodies, e.g., vertebrae and/or vertebral discs, of the subject. In these embodiments, the processor 120 can analyze the image scan to locate a particular point (e.g., x, y, z coordinate) of each vertebral body in the subject. For example, the particular point can be the point where the center of the spinal canal and a plane through the disc immediately below the vertebral body intersect. It should be appreciated that other points corresponding to a vertebra can be used. The processor 120 can be further configured to identify other types of markers as well. For example, the processor 120 can be configured to identify the skin of the subject, fascia of the subject, ribs of the subject, or any other organ, bone, tissue, or muscle. Furthermore, while some components can be referenced using one or more points, other components may be referenced with one or more lines, curves, polygons, or combinations thereof.

Figure 3:
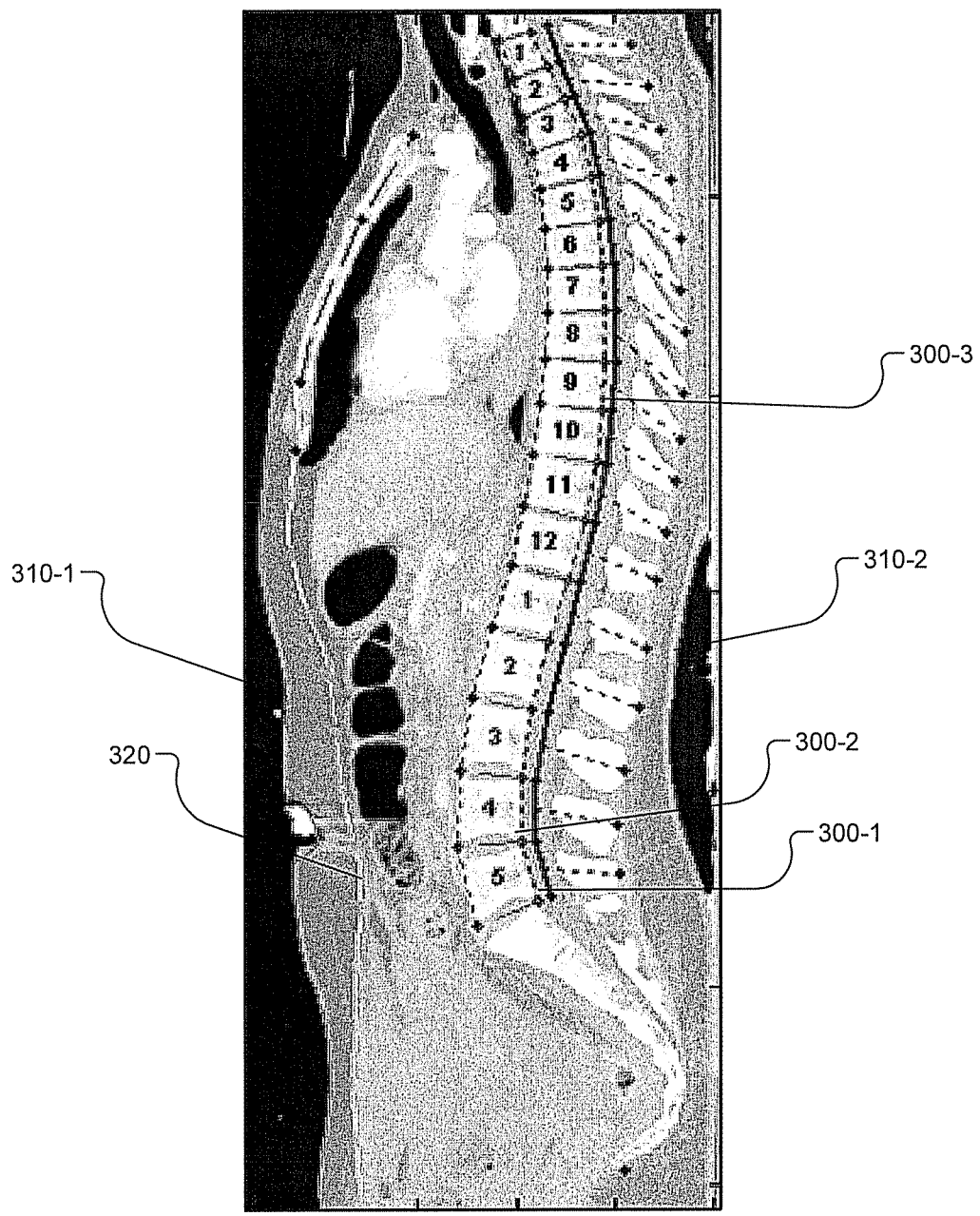
FIG. 3 is a schematic illustrating a cross-sectional view of an image scan.

Referring now to FIG. 3, a cross-sectional view of an image scan 130 is illustrated. The cross-sectional sagittal view is taken from an (y, z) plane of the image scan 130. In the example of FIG. 3, the processor 120 has identified a plurality of markers, including vertebral bodies, e.g., vertebral body markers 300-1, 300-2, and 300-3, skin markers, e.g., skin markers 310-1, 310-2, and a fascia marker 320. In the illustrative example, the vertebral body markers 300-1, 300-2, and 300-3 can be represented by one or more points, the skin markers 310-1 and 310-2 can be represented by one or more polygons, and the fascia marker 320 can be represented by one or more lines. It is noted that the processor 120 can determine other types of markers, including but not limited to rib markers, pelvic markers, and kidney markers.

Referring back to FIG. 1, once the processor 120 identifies a location of a marker, the processor 120 can generate a database entry corresponding to the marker and can store the database entry in the measurements database 150. The database entry can include fields which identify the marker. For example, the database entry can include fields for a marker identifier indicating the type of marker, one or more points and/or shapes that define the location of the marker, and the scan identifier indicating the image scan in which the marker was identified. For example, a database entry corresponding to a vertebral body marker can be defined as:

Vertebral Body Marker {
Scan ID [string]
Marker ID [string]
Location [point]
}.

Thus, if the intersection of the vertebral disc corresponding to the L-5 vertebra and the center of the vertebral canal intersect at the point (14, 15, 20) in image scan 1234, a vertebral marker database entry can be generated that indicates the scan id is 1234, the marker identifier is L-5, and the location is (14, 15, 20). The processor 120 can then store the generated database entry in the measurements database 150. The foregoing example of a database entry is not intended to be limiting. It is noted that additional fields can be included in the database entry.

Figure 4:
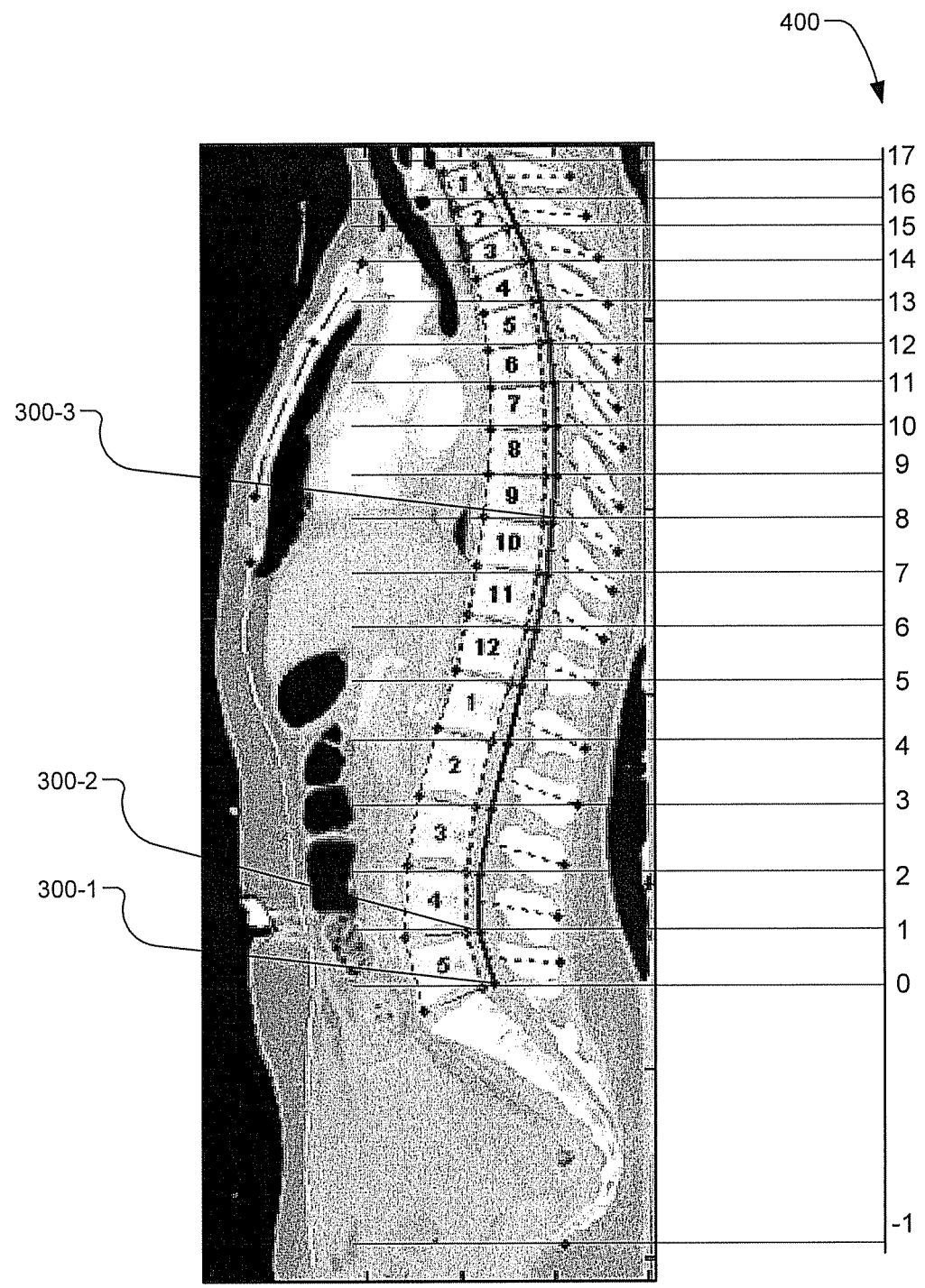
FIG. 4 is a schematic illustrating a vertebral body coordinate system in relation to the cross-sectional view of the image scan depicted in FIG. 3.

As mentioned, the markers in an image scan 130 can be used to define one or more coordinate systems. In the context of vertebral body markers, the vertebral body markers can collectively define a vertebral level coordinate system. FIG. 4 illustrates an example of a vertebral level coordinate system 400. In the illustrated example, each vertebral body marker, e.g., 300-1, 300-2, and 300-3, corresponds to a different level in the vertebral level coordinate system 400, e.g. VLC0, VLC1, and VLC8, respectively. As should be appreciated, the locations of the vertebral markers with respect to an image scan can vary from image scan to image scan. Thus, by using the vertebral level coordinate system 400, specific locations of the volume of a subject can be referenced using a vertebral level coordinate. For example, a vertebral level coordinate of 0 can correspond to an image slice 200 where the marker for the L-5 vertebra is located. Similarly, a vertebral level coordinate of 2.5 can correspond to an image slice 200 halfway between the image slices 200 where the L-3 and the L-2 vertebrae are located. As can be appreciated from the foregoing, vertebral level coordinates can be used to reference relative locations across many different image scans 120, even when there is a low degree of uniformity between the image scans 120, e.g., subjects of different heights.

Figure 5:
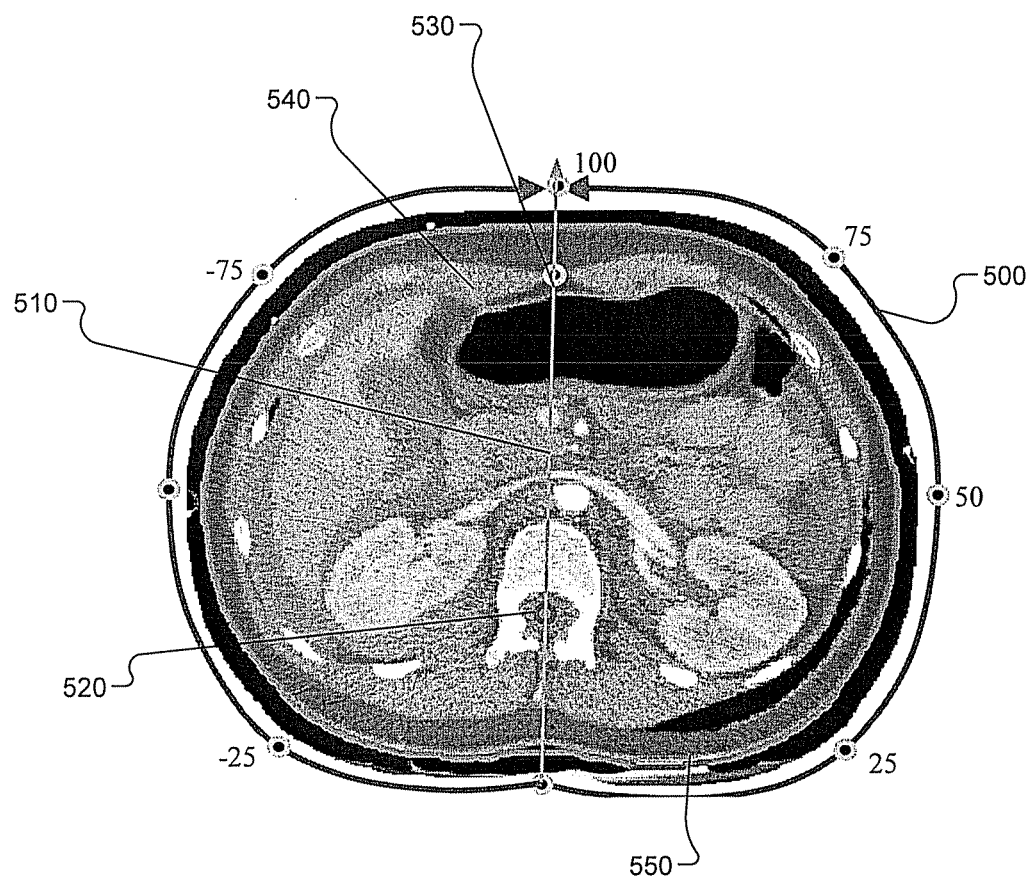
FIG. 5 is a schematic illustrating a body surface coordinate system in relation to an image slice.

It is noted that if other markers are stored, additional coordinate systems can be implemented to reference locations within the image scans 120. For example, one coordinate system is a body surface coordinate system. FIG. 5 illustrates an example of a body surface coordinate system 500. When a specific image slice 200 is taken (at, for example, a given vertebral level component), the spinal location is known. If only the spinal canal point is known, it may be difficult for the processor 120 to determine the subject's true "anterior" direction (it would only be "forwards" in the image scan if the subject were perfectly symmetrical and lying perfectly straight in the image scan 130). To determine the body's true anterior direction, a second marker may be located. For example, the processor 120 can identify a vector 510 extending from the spinal canal 520 to a central anterior seam 530 (e.g., the abdominal linea alba) of the subject's fascia 540. With this vector 510 in place it is possible to separate the body into left/right regions. With the addition of a line 550 defining the skin encircling the body, it is possible to define a body surface coordinate system.

The body surface coordinate system 500 can have a zero location at the intersection of the anterior-direction vector 510 and the skin line 550. The body surface coordinate system 500 can define a percentage distance around the body on either side such that the intersection of the anterior-direction vector 510 and the skin line 500 at the front of the body is one hundred percent. The coordinate system runs symmetrically on the left and right sides, such that a body surface coordinate of +25 means "the location at 25 percent around the left side of the body", where as a body surface coordinate of −60 means "the location at 60 percent around the right side of the body". When combined with the vertebral level coordinate system, it is possible to reference a single location along the surface of a subject using a vertebral level coordinate and a body surface coordinate. For example, a location corresponding to "20 percent around the left side of the body, half-way between the T12 and T11 vertebral levels" can be referenced by a coordinate: [VLC 5.5, BSC 20]. It should be appreciated that while percentages are used, a body surface coordinate can be referenced by an angle measure, e.g., radians or degrees.

The vertebral level coordinate system 400 and the body surface coordinate system 500 described above are merely examples of body coordinate systems. It is noted that other body coordinate systems, such as rib coordinate systems and a pelvic coordinate system can be used as well and are within the scope of the disclosure. To define other body coordinate systems, the processor 120 can identify other types of markers corresponding to the other body coordinate systems. For example, in identifying pelvic markers, the processor 120 can identify one or more predetermined components of the pelvis, including the iliac crest, pubic symphysis, and acetabulum.

Appendix A illustrates different types of markers which can be used in various combinations to define other body coordinate systems. The examples of Appendix A are not intended to be limiting. Furthermore, while the descriptions of the markers are provided, the descriptions are provided for example. One having skill in the art would be able to derive other descriptions of markers after consulting the examples of Appendix A.

Once the processor 120 has determined the markers for an image scan 130, the image scan 130 can be said to have been indexed. The image scan data, including the image scan 130 and the image scan identifier, can be stored in the image scan datastore 140. In this way, each image scan 130 is linked to its corresponding markers by the image scan identifier. Thus, when a measurement is to be taken with respect to multiple image scans, a user (e.g., human or computer) can reference locations within the image scans using one or more body coordinate systems. For example, if a researcher wishes to measure the cross-section of fat corresponding to the L-5 vertebra of all of the image scans 120 stored in the image scan datastore 140, the processor 130 can retrieve image slices 200 of the image scans 130 that correspond to the vertebral level coordinate 0. For each image scan 130 that is to be analyzed, the processor 120 can retrieve the vertebral body markers sharing the scan identifier of the image scan 130. The processor 120 can then determine the z-coordinate corresponding to the vertebral level coordinate, e.g., VLC0, from the one or more vertebral body markers. The processor 120 can then retrieve the image slice 200 corresponding to the z-coordinate. The processor 120 can locate the fat area depicted in the retrieved image slice 200, either automatically or with the assistance of a user, and can measure the cross-sectional area of the fat in the retrieved image slice 200. The processor 120 can generate a database entry corresponding to the measurement, which can be stored in the measurements database 150. A measurement entry can include a scan identifier, one or more body coordinates corresponding to the relative location where a measurement was taken, and the measurement. As can be appreciated, more complex measurements can be taken using a plurality of body coordinates.

Figure 6:
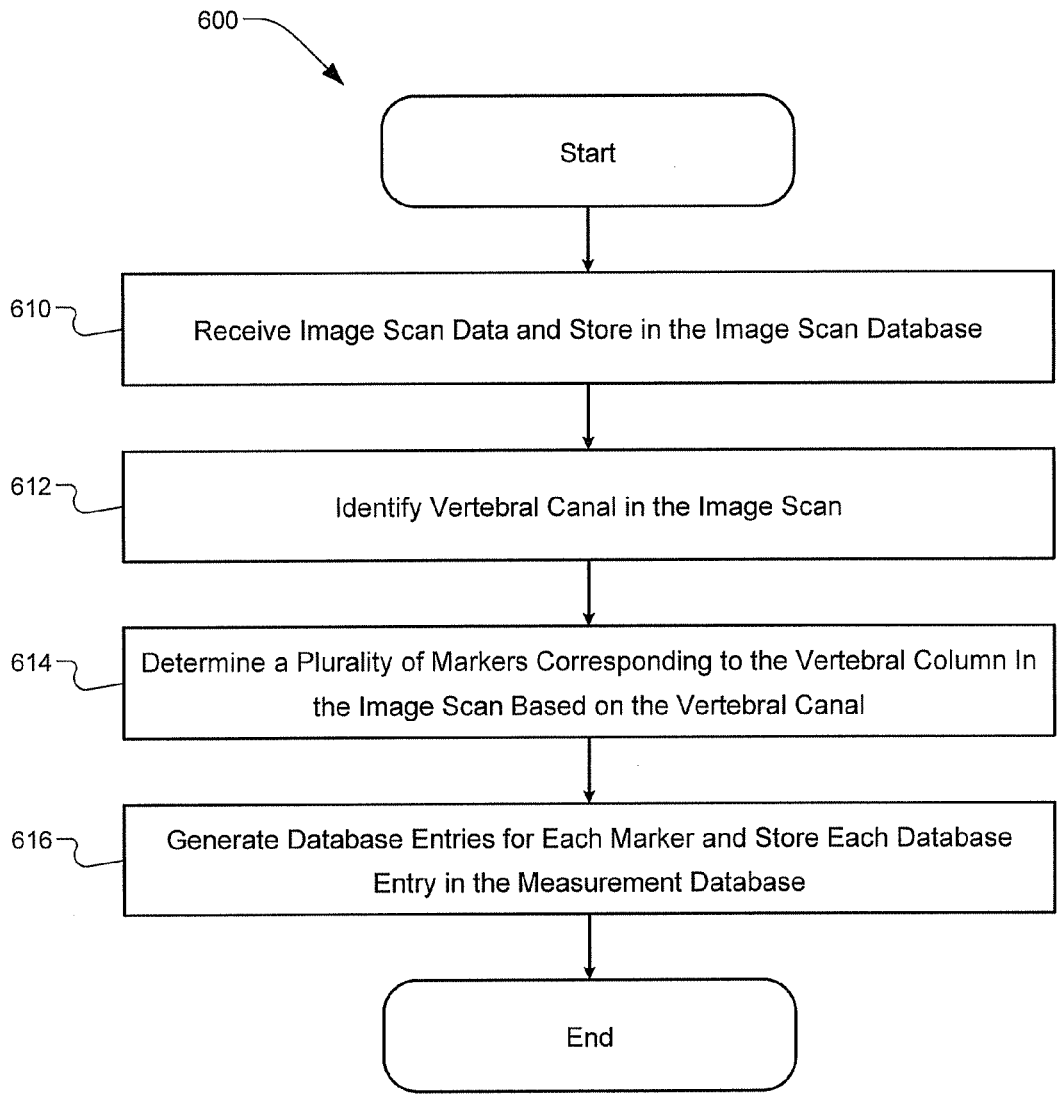
FIG. 6 is a flow chart illustrating an exemplary method for indexing an image scan.

Referring now to FIG. 6, an example method 600 for indexing an image scan using vertebral markers is illustrated. At operation 610, the processor 120 receives image scan data representing a volume of a subject. As described above, the image scan data can include an image scan 130 and metadata such as a scan identifier. The processor 120 can store the image scan data in the image scan datastore 140.

Upon receiving an image scan, the processor 120 can identify the vertebral canal in the image scan, as shown at 612. The processor 120 can identify the vertebral canal in any suitable manner. In some embodiments, the processor 120 can be configured to perform spinal or vertebral extraction. An example of spinal extraction is described in Yao et al, "Automated Spinal Column Extraction and Partitioning," (ISBI 2006). To perform vertebral extraction, the processor 120 can begin by identifying any potential bones in the image scan 130 based on the differing intensities in the image scan 130. A 3-dimensional distance map can be calculated from the located bones. The processor 120 can then identify candidate centers of the vertebral canal as planar local maxima in the distance map that are closer than a predetermined distance, e.g., 20 mm, from the identified bone. The processor 120 can connect the candidate centers by image ridges in the distance map, and can fit an estimated 3-dimensional curve relative to the image ridges. The estimated 3-dimensional curve approximates the shape of the vertebral canal. Thus, any candidate centers that were inadvertently labeled as centers, e.g., intestines, can be removed from consideration as the image ridges are unlikely to resemble the 3-dimensional curve. It is noted that a graphical user interface can allow a human user to adjust the final curve manually in the sagittal and coronal planes. Using interpolated slices perpendicular to the vertebral canal, the axial rotation of the vertebral column as a function of caudal level is specified as the angle of the axis of symmetry of slice pixels within a second predetermined distance, e.g., 40 mm, of the vertebral canal center.

Once the vertebral canal is identified, the processor 120 can identify a plurality of markers corresponding to the vertebral column based on the identified vertebral canal, as shown at operation 614. The processor 120 can identify the plurality of markers in any suitable manner. For example, the processor 120 can generate a curved planar reformation in the sagittal plane based on the identified vertebral canal, aligned with the local axial twist. Traveling cranially along the curved planar reformation in 1 mm increments from the lowest spinal level imaged, the processor 120 can obtain density samples between 5 and 30 mm anterior to the vertebral canal. Peaks in this signal correspond to vertebral body endplates, and hypodense troughs correspond to disc spaces. Peaks and troughs are then represented to the user as initial labeling of vertebral levels (starting at the L-5 vertebral body). It is noted that the human user can manually correct any labeling errors that the processor 120 may have made. For example, if the lowest portion of the image scan begins at L-4, the processor 120 may inadvertently label the vertebral body L-4 as L-5. The human user can label the vertebral body as L-4. At each specified vertebral level, the processor 120 can record one or more 3-dimensional points of the vertebral body. For example, the processor 120 can record the location where the medial axis of the vertebral body intersects the vertebral canal. It should be appreciated that the processor 120 can implement other techniques for determining the plurality of markers, and such techniques that are within the scope of the disclosure.

The processor 120 can then generate a plurality of database entries, each database entry corresponding to a different vertebral marker, as shown at operation 616. The processor 120 can include the point corresponding to a marker in a database entry, as well as a label of the marker and a scan identifier. The processor 120 can then store the plurality of database entries representing the plurality of markers in the measurements database 150. Once the processor 120 has defined the plurality of markers for an image scan, the image scan has been indexed. As discussed above, the plurality of markers collectively define a body coordinate system. In the present example, the plurality of markers defines the vertebral level coordinate system 400. It is to be understood that only the relevant steps of the methodology are discussed in relation to FIG. 6, but that other software-implemented instructions may be needed to control and manage the overall operation of the system.

The foregoing method 600 is provided for example only and not intended to be limiting. Furthermore, the techniques disclosed are explained with respect to identifying vertebral markers. It should be appreciated, that other techniques may be used to identify other types of markers.

Figure 7:
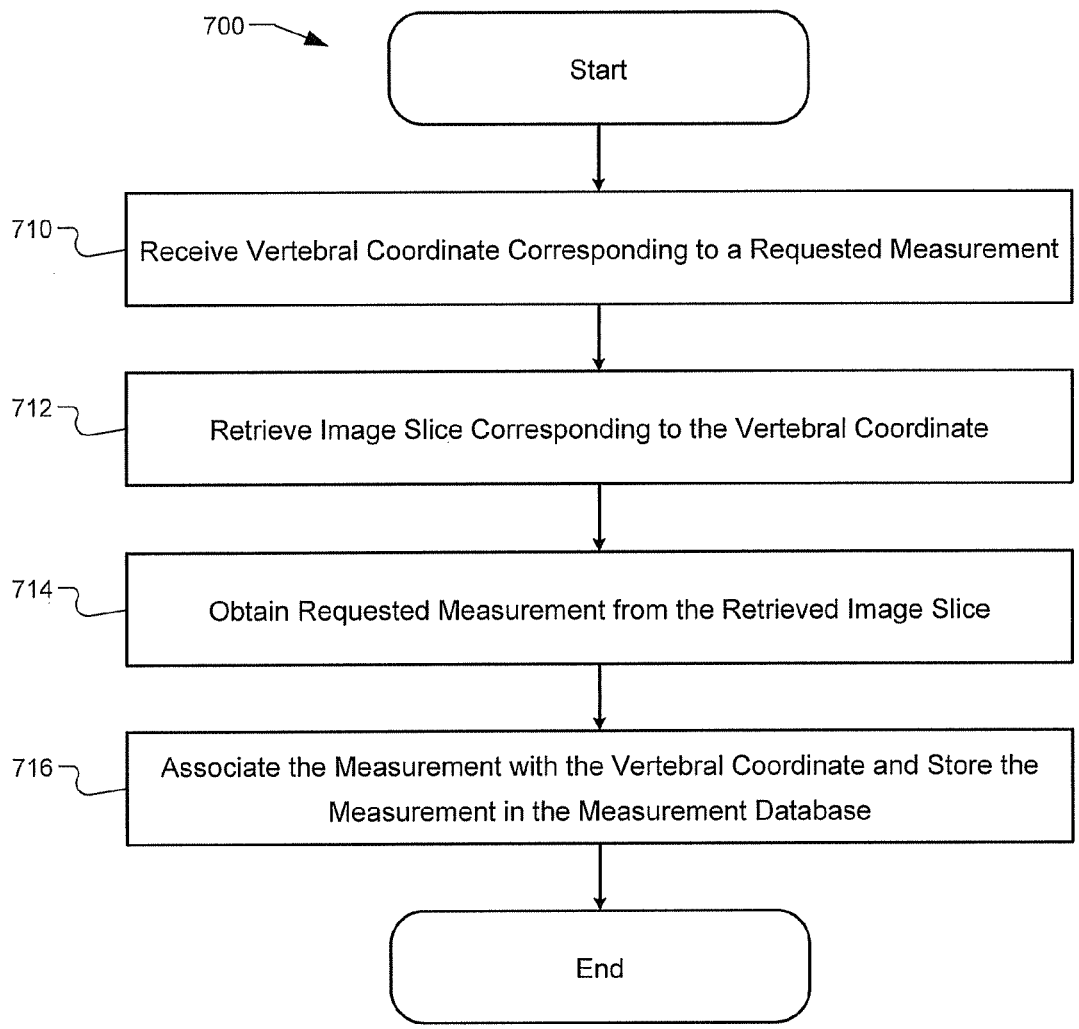
FIG. 7 is a flow chart illustrating an exemplary method for obtaining a measurement using a body coordinate system.

Referring now to FIG. 7, a method 700 for obtaining a measurement using a body coordinate system. In the example provided, the body coordinate system is the vertebral coordinate system. At operation 710, the processor 120 receives a request to perform a measurement and a vertebral level coordinate corresponding to a requested measurement. For example, a user may request that a subject's cross-sectional area of fat at a particular vertebral level, e.g., vertebral level coordinate 2.5, be measured.

At operation 712, the processor 120 retrieves one or more image slices 200 corresponding to the requested vertebral coordinate. The processor 120 can determine which image slices to retrieve by looking up the vertebral body markers corresponding to the scan identifier of the image scan being analyzed. As discussed previously, the vertebral body markers each have at least one point defining the location of the vertebral marker in the image scan. The processor 120 can determine which image slice 200 or slices to retrieve based on the z-coordinates of the requested vertebral coordinate. The processor 120 can determine the z-coordinate corresponding to the requested vertebral level coordinate based on the vertebral body markers corresponding to an image scan 130. For example, if the vertebral coordinate is VLC1, the processor 120 can obtain the z-coordinate of the L-4 vertebral marker of a particular image scan by retrieving the vertebral body marker database entry having a marker identifier indicating the L-4 vertebral body and a scan identifier corresponding to the particular image scan. If, however, the vertebral coordinate is VLC2.5, the processor 120 can obtain the coordinates of the L-3 and L-2 vertebral markers of the particular image scan, and can determine the z-coordinate that is halfway between the L-2 and L-3 marker. Once the processor 120 has determined the z-coordinate, the processor 120 retrieves the image slice or slices corresponding to the z-coordinate.

The processor 120 can then determine the requested measurement from the retrieved image slice, as shown at operation 714. It is noted that because the researcher can define any measurement, operation 714 will vary depending on the requested measurement. Once the processor 120 has determined the measurement, the processor 120 can associate the measurement with the requested vertebral coordinate and store the measurement in the measurement database 150, as shown at operation 714. In some embodiments, the processor 120 can generate a measurement database entry indicating the measurement, the vertebral level coordinate corresponding to the measurement, and the scan identifier corresponding to the measurement. The processor 120 can store the measurement database entry in the measurements database 150.

As mentioned there are various measurements that can be taken using body coordinate systems. Appendix B illustrates a non-exhaustive list of measurements that can be taken using one or more body coordinate systems.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known procedures, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

As used herein, the term module may refer to, be part of, or include: an Application Specific Integrated Circuit (ASIC);

an electronic circuit; a combinational logic circuit; a field programmable gate array (FPGA); a processor or a distributed network of processors (shared, dedicated, or grouped) and storage in networked clusters or datacenters that executes code or a process; other suitable components that provide the described functionality; or a combination of some or all of the above, such as in a system-on-chip. The term module may also include memory (shared, dedicated, or grouped) that stores code executed by the one or more processors.

The term code, as used above, may include software, firmware, byte-code and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present invention.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

APPENDIX A

The following is a list of the geometries that can be stored in the database.

```
--== ABDINJURY ==--
    LIVERINJURYVOL                      [
    SPLEENINJURYVOL                     [
--== CHEST ==--
    RT3MAJORPECVENTRALLINE              [
    LT3MAJORPECVENTRALLINE              [
    RT4MAJORPECVENTRALLINE              [
    LT4MAJORPECVENTRALLINE              [
--== CSPINE ==--
    SPINALCANALLINE                     [
    LFORAMENPTS                         [
    RFORAMENPTS                         [
--== CVERTEBRA ==--
    LINFFACETSURFACE                    [
    RINFFACETSURFACE                    [
    INFDISCPOSTPT                       [
    LSUPFACETSURFACE                    [
    RSUPFACETSURFACE                    [
    INFDISCSURFACE                      [
    INFDISCSCPT                         [
    MIDVBSCPT                           [
    SPINOUSPROCESSPOSTPT                [
    INFDISCANTPT                        [
--== FASCIA ==--
    CENTRALANTERIORSEAM                 [CURVE ]
        A line down the center of the body from the
    sternum to the pubis, traveling along the fascial
    plane (linea alba) between the left and right rectus
    muscles.
```

APPENDIX A-continued

The following is a list of the geometries that can be stored in the database.

```
XYPHOIDPROCESSANCHORPT            [POINT ]
    The inferiormost tip of the sternum's xyphoid
process. This point anchors the top of the fascia's
central anterior seam.
PUBISANCHORPT                     [POINT ]
    The center of the pubic symphysis. This anchors
the bottom of the fascia's central anterior seam.
SUPERFICIALPTS                    [POINTS]
    A point cloud of "handles" around the fascial
envelope. These handles can be moved by users.
SUPERFICIALLINES                  [CURVES]
    A set of closed curves wrapping around the
fascial envelope. These lines join the SUPERFICIALPTS
into closed contours.
LRECTUSLATERALSEAM                [CURVE ]
    The left edge of the rectus muscle running down
the abdomen.
RRECTUSLATERALSEAM                [CURVE ]
    The right edge of the rectus muscle running down
the abdomen.
--== KIDNEYS ==--
RADRENALVOL                       [
LADRENALVOL                       [
LSEGBBOXPTS                       [
RSEGBBOXPTS                       [
LSEGCENTROIDPT                    [
RSEGCENTROIDPT                    [
LKIDNEY                           [
RKIDNEY                           [
LBBOXPTS                          [
RBBOXPTS                          [
LCENTROIDPT                       [
RCENTROIDPT                       [
--== LIVER ==--
AORTA                             [
VENACAVA                          [
ANTERIORFALCIFORMLIGAMENT         [
SUPERIORGALLBLADDERTIP            [
INFERIORTIPCAUDATELOBE            [
POSTERIORFALCIFORMLIGAMENT        [
PORTALVEIN                        [
MEDIALLIVERPT                     [
LATERALLIVERPT                    [
SUPERIORLIVERPT                   [
LIVEROBJECT                       [
BBOXPTS                           [
SPLEENBBOXPTS                     [
INFERIORLIVERPT                   [
ANTERIORLIVERPT                   [
POSTERIORLIVERPT                  [
LIVERSEG                          [
AXIALSUPERIORCONTOUR              [
AXIALINFERIORCONTOUR              [
CORONALANTERIORCONTOUR            [
CORONALPOSTERIORCONTOUR           [
SAGITTALLEFTCONTOUR               [
SAGITTALRIGHTCONTOUR              [
--== MUSCLE_ERECTOR_SPINAE ==--
RT10CONTOUR                       [
LT10CONTOUR                       [
--== MUSCLE_PSOAS ==--
RL4AXIALCONTOUR                   [POLYLINE]
    A closed contour drawn around the (right) psoas
muscle at the level of L4.
LL4AXIALCONTOUR                   [POLYLINE]
    A closed contour drawn around the (left) psoas
muscle at the level of L4.
--== PELVIS ==--
RACETABULARRIMPTS                 [ ]
SACRALTIPPT                       [POINT ]
    A landmark at the tip of the coccyx.
PELVISORIGINPT                    [POINT ]
LACETABULARRIMPTS                 [ ]
RFEMORALHEADCENTROIDPT            [POINT ]
    A landmark at the center of the right femoral
head.
RWINGSUPERIORMOSTPT               [POINT ]
CENTRALANTERIORSACRALSEAM         [ ]
SACRAL4FORAMINALRTB               [ ]
LACETABULARCENTROIDPT             [POINT ]
RACETABULARCENTROIDPT             [POINT ]
PUBICRAMIFXPTS                    [ ]
LACETABULARFXPTS                  [ ]
RACETABULARFXPTS                  [ ]
LSUPWINGCURVE                     [CURVE ]
RSUPWINGCURVE                     [CURVE ]
LPUBICPROCESSPT                   [POINT ]
RPUBICPROCESSPT                   [POINT ]
LWINGLATERALMOSTPT                [POINT ]
RWINGLATERALMOSTPT                [POINT ]
LWINGSUPERIORMOSTPT               [POINT ]
LISCHIUMINFERIORMOSTPT            [POINT ]
RISCHIUMINFERIORMOSTPT            [POINT ]
PUBISCENTRALPT                    [POINT ]
    A landmark placed in the center of the pubic
symphysis.
LANTSUPILIACSPINEPT               [POINT ]
RANTSUPILIACSPINEPT               [POINT ]
    A landmark at the tip of the superior-anterioriliac
spine - a vehicle seatbelt restraint location.
LSUPPUBICRAMICENTROIDPT           [POINT ]
    A landmark at the tip of the superior-anterioriliac
spine - a vehicle seatbelt restraint location.
RSUPPUBICRAMICENTROIDPT           [POINT ]
LGTROCHANTERLATERALMOSTPT         [POINT ]
RGTROCHANTERLATERALMOSTPT         [POINT ]
LFEMORALHEADCENTROIDPT            [POINT ]
--== RIB ==--
ICMDEEPLINES                      [CURVE ]
    A set of points halfway between a pair of ribs
that define the deep boundary of the intercostal
muscles.
ICMSUPLINES                       [CURVE ]
    A set of points halfway between a pair of ribs
that define the superficial boundary of the
intercostal muscles.
PROXIMALENDPT                     [POINT ]
    Landmark specifying the connection point between
this rib and the spine.
DISTALENDPT                       [POINT ]
    Landmark specifying the tip of this rib.
CENTROIDCURVE                     [CURVE ]
    The driving geometry of a rib. A curve running
down the rib center from the spine to the tip of the
rib.
NUBPT                             [POINT ]
    A landmark at the "tubercle" rib location (now
defunct).
--== RIBCAGE ==--
RIBDISTALENDPTS                   [
--== SHOULDERS ==--
LCLAVICLEDISTALPT                 [
LCLAVICLEPROXIMALPT               [
RCLAVICLEDISTALPT                 [
RCLAVICLEPROXIMALPT               [
LCLAVICLEFXPT                     [
RCLAVICLEFXPT                     [
--== SKIN ==--
PERIMETERCURVES                   [MULTIPOLYGON]
    A set of axial closed contours defining the skin
surface.
CENTRALANTERIORSEAM               [LINE  ]
    The line running down the central plane (as
defined via the fascia centralAnteriorSeam) of the
body at the intersection of this plane and skin at the
front of the body.
CENTRALPOSTERIORSEAM              [LINE  ]
    The line running down the central plane (as
defined via the fascia centralAnteriorSeam) of the
body at the intersection of this plane and skin at the
back of the body.
```

APPENDIX A-continued

The following is a list of the geometries that can be stored in the database.

```
--== STERNUM ==--
    CENTROIDCURVE                          [CURVE ]
        A curve running down the center (medial and
        saggital) of the sternum from the inferior border of
        the sternum body to the sternal notch (top of
        manubrium).
    XYPHOIDPROCESSPT                       [POINT ]
        A landmark at the inferiormost tip of the xphoid
        process.
    BODYINFPT                              [POINT ]
        A landmark at the intersection of the sternum
        body and the xyphoid process.
    BODYSUPPT                              [POINT ]
        A landmark at the intersection of the sternum
        body and the manubrium.
    MANUBRIUMSUPPT                         [POINT ]
        A landmark at the sternal notch at the superior
        aspect of the manubrium.
    FXPT                                   [POINT ]
        Storage for the "center of mass" of any potential
        sternum fractures.
    FXPTS                                  [MULTIPOINT]
        Storage for all potential sternum fractures.
--== VASCULATURE ==--
    SUPCELIACBRANCHPT_MAN                  [
    ARTERIALVOL                            [
    ARTERIALPTS                            [
    ARTERIALENDPTS                         [
    ARTERIALBRANCHPTS                      [
    AORTICBIFURPT                          [
    LFEMORALARTERYCUTPT                    [
    RFEMORALARTERYCUTPT                    [
    AORTICBIFURPT_MAN                      [
    RINFINTILIACBRANCHPT                   [
    LINFINTILIACBRANCHPT                   [
    RINFINTILIACBRANCHPT_MAN               [
    INFINTILIACBRANCHPT_MAN                [
    RRENALBRANCHPT                         [
    LRENALBRANCHPT                         [
    RRENALBRANCHPT_MAN                     [
    LRENALBRANCHPT_MAN                     [
    SMABRANCHPT                            [
    SMABRANCHPT_MAN                        [
    CELIACBRANCHPT                         [
    CELIACBRANCHPT_MAN                     [
    LSUBCLAVIANBRANCHPT                    [
    LSUBCLAVIANBRANCHPT_MAN                [
--== VASC_AORTA ==--
    L1CENTROIDPT                           [
    CENTROIDCURVE                          [
    ANTERIORCURVE                          [
--== VERTEBRA ==--
    LOWERDISCSCPT                          [POINT ]
        The point at the intersection of the center of
        the spinal canal and a plane through the disc
        immediately below this vertebra.
    LOWERDISCANTPT                         [POINT ]
        The anterior point at the center of the vertebral
        body at the plane of the lower disc.
    LOWERDISCPOSTPT                        [POINT ]
        The posterior point at the center of the
        vertebral body at the plane of the lower disc.
        LTPPT                              [POINT ]
            The tip of the left transverse process.
        RTPPT                              [POINT ]
            The tip of the right transverse process.
        SPINOUSPROCESSPOSTPT               [POINT ]
            The posterior-most point on the spinous process.
--== SCOUTS ==--
    LBOUNDARYCURVE                         [
    RBOUNDARYCURVE                         [
    FBOUNDARYCURVE                         [
    BBOUNDARYCURVE                         [
--== LUNGS ==--
    RLUNGVOL                               [
    LLUNGVOL                               [
    CENTROIDPT                             [
    CENTROIDPT                             [
```

APPENDIX A-continued

The following is a list of the geometries that can be stored in the database.

```
--== SPLEEN ==--
    SPLEENVOL                              [
    BOXPTS                                 [
    CENTROID                               [
```

APPENDIX B

The following is an example structure of a measurement table identifying example measurements that can be taken using one or more body coordinate systems. With the exception of Age, Height, Weight, BMI, all of these measurements rely on one or more body coordinate systems. Most of these measures rely specifically on one or more of our defined coordinate systems. For example, all Psoas Muscle measures are taken at the L4 vertebra level (VLC=1), all "per vertebra" measures are taken at every vertebral level (VLC=0-through-17), and spine-to-skin or spine-to-fascia are additionally taken at BSC=0 or 100.

AGE [yrs] Age of the individual at time of scan

HEIGHT [m] Height of the individual

WEIGHT [kg] Weight of the individual

BMI [kg/m^2] BMI of the individual

L_PSOASL4AREA [mm^2] Cross sectional area of the (left side) psoas muscle at the L4 vertebral level R_PSOASL4AREA [mm^2] Cross sectional area of the (right side) psoas muscle at the L4 vertebral level TOTAL_PSOAS_AREA [mm^2] Cross sectional area of the psoas muscle at the L4 vertebral level (combined left+right)

L_PSOASL4MEANHU [HU] Average pixel intensity inside psoas muscle region (left)

R_PSOASL4MEANHU [HU] Average pixel intensity inside psoas muscle region (right)

PSOAS_HU [HU] Average pixel intensity inside psoas muscle region (left+right sides combined)

L_PSOASL4STDDEVHU [HU] Standard deviation of pixel intensies inside psoas muscle region (left)

R_PSOASL4STDDEVHU [HU] Standard deviation of pixel intensies inside psoas muscle region (right)

LEAN_PSOAS [HU*mm] Psoas cross sectional area multiplied by "psoas pixel intensity normalized between −85 and +85 HU"

AORTA_CALC_PCNT_WALL [pcnt] Percentage of aorta wall exhibiting calcification between L3-L1 region DIST_ASISPT2ASISPT [mm] Distance between left and right anterior superior iliac spines (ASIS)

DIST_FHPT2FHPT [mm] Distance between left and right femoral head centoid locations DIST_WINGLATPT2WINGLATPT [mm] Lateral size of bony pelvis "bounding Box"

PHEIGHT [mm] Vertical size of bony pelvis "bounding Box"

LFEMORALHEADRADIUS [mm] Radius of best-fit sphere to the left femoral head

RFEMORALHEADRADIUS [mm] Radius of best-fit sphere to the right femoral head

FEMORALHEADRADIUS [mm] Average radius of left/right femoral heads, or radius of uninjured side with unilateral FH injury DIST_LASISPT2PUBISPT [mm] Distance from ASIS (left) to pubic symphysis DIST_RASISPT2PUBISPT [mm] Distance from ASIS (right) to pubic symphysis ANG_LASIS_PUBIS_RASIS [deg] Angle subtended between 3 landmarks "Left ASIS→Pubi→Right ASIS"

The following is a list of 33 variables that are reported "per vertebra".

Each person will have at most 17 vertebras visible in the scan (L5 through L1, T12 through T1).

Therefore these 33 measures per vertebra will produce 561 data points for any given person:

BODYDEPTH [mm] Depth of the body (anterior/posterior) at this vertebral level, measured in "bounding box" style BODYWIDTH [mm] Width of the body (lateral) at this vertebral level, measured in "bounding box" style RIBCAGEDEPTH [mm] Depth of the ribcage at the planar location of this vertebral level RIBCAGEWIDTH [mm] Width of the ribcage at the planar location of this vertebral level TOTALBODYAREA [mm^2] Cross sectional area of the body at this vertebral level FASCIAAREA [mm^2] Cross sectional area of the visceral cavity (defined by the superficial fascia) at this vertebral level SUBCUTFATAREA [mm^2] Cross sectional area of the subcutaneous region of the body (outside the visceral cavity)

VISCERALFATAREA [mm^2] Cross sectional area of fat-intensity pixels inside the visceral cavity SUBCUTFATAREA [mm^2] Cross sectional area of fat-intensity pixels in the subcutaneous region HEIGHT [mm] Height of the body "slab" for this Vertebra—given to turn cross sectional areas into volumes FASCIAECCENTRICITY [ratio] Eccentricity of an ellipse having the same second-moments of the fascia region. (Ratio of major-axis length to the distance between ellipse foci). A circle has eccentricity of 0, while a line has eccentricity of 1

VB2FRONTSKIN [mm] Distance from the anterior aspect of the vertebral body out to the skin at the front of the body VB2FASCIA [mm] Distance from the anterior part of the vertebral body out to the fascia at the medial body plane (linea alba)

SP2BACKSKIN [mm] Distance from posterior tip of the spinous process posteriorly to the skin at the back of the body DIST_ANTPT2POSTPT [mm] Size of the vertebral body (anterior to posterior)

DIST_INFSCPT2SUPSCPT [mm] Distance along the spinal canal from this vertebra to its superior neighbour DIST_INFANTPT2SUPANTPT [mm] Height of the vertebral body at anterior aspect DIST_INFPOSTPT2SUPPOSTPT [mm] Height of the vertebral body at posterior aspect ANG_X_WRTXZ [deg] Pose of this vertebra in the scan (roll)

ANG_Y_WRTYZ [deg] Pose of this vertebra in the scan (pitch)

ANG_X_WRT_INFVB [deg] Angle of this vertebra angle (side-to-side rotation) with respect to its inferior vertebra ANG_Y_WRT_INFVB [deg] Angle of this vertebra angle (forward/backwards or flex./extension) with respect to its inferior vertebra SPYTOPOSTMOSTY [mm] Distance posteriorly between this Vertebra's spinous process tip and the posterior-most spinous process tip on this individual BMDHUVBALIGNED [HU] Average pixel intensity inside a mid-vertebral core sample ANTCORTFWHM [HU] The Houndsfield Unit value at half the maximum peak of a sample signal across the anterior cortical bone ANTCORTHMHU [HU] "Anterior Cortical Half-Maximum Hounsfield Unit"—HU level at half-max of the bone signal peak ANTCORTFWBYHM [HU*mm] The "Full-width-multiplied-by-half-max" of the avg. cortical bone signal (Newman—1998, Prevrhal—1999)

ANTCORTFWHMBYHM_STD [HU*mm] Std. Dev. from all 60 "Full-width-by-half-max" measurements (at 10 increments in a 600 anterior wedge)

RECTUSXSECAREA [mm^2] Cross sectional area of the rectus muscle (left+right) at this vertebral level RECTUSVOLUPTOVB [mm^3] Volume of the rectus muscle measured from the pubis up to this vertebral level PSPXSECAREA [mm^2] Cross sectional area of the paraspinous muscle group at this vertebral level PSPVOLOFVB [mm^3] Volume of paraspinous muscle group between this vertebra and its superior neighbour LUNGXSECAREA [mm^2] Cross sectional area of the lungs region at this vertebral level The following is a list of 5 variables that are reported "per rib".

Each person will have at most 24 ribs visible in the scan (ribs 1 through 12, left and right sides).

Therefore these 5 measures per rib will produce 120 data points for any given person:

RIBLENGTH [mm] Length of a curve running along centroid of the rib

RIBDEPTH [mm] Anterior-posterior dimension of a rib "bounding box"

RIBLATWIDTH [mm] Lateral distance from the spinal canal to the lateralmost point on the rib RIBANGLE [deg] Angle along diagonal of the rib "bounding box" with respect to vertical. Vertically hanging ribs have zero angle, horizontally oriented ribs have 90 deg angle.

RIBCURVATURE [mm] Radius of a planar circle fitted to 20 equally spaced points along the length of the rib The following is a list of 6 variables that are reported "per rib per location".

Each person will have at most 240 rib per locations visible in the scan (10 equally spaced locations along 24 ribs).

Therefore these 6 measures per rib per location will produce 1440 data points for any given person:

RIBLOCANGLE [deg] Angle of rib tangent with respect to vertical at rib location

RIBLOCCURVATURE [mm] Radius of a planar circle fitted to local rib curve

RIBLOCXSECAREA [HU] Average cross sectional area of rib at rib location

RIBLOCDENSITY [HU] Average pixel intensity within rib boundary at rib location

ICMLOCTHICKNESS [mm] Thickness measured across intercostal muscle space between this rib and its superior neighbour at rib location.

ICMLOCHU [HU] Average pixel intensity of intercostal muscle space between this rib and its superior neighbour at rib location.

| Summary: | |
|---|---|
| Per person | 24 * 1 measures = 24 |
| Per vertebra | 33 * 17 measures = 561 |
| Per rib | 5 * 24 measures = 120 |
| Per rib per location | 6 * 240 measures = 1440 |
| Total of 2145 measures reported for each person | |

What is claimed is:

1. A computer-implemented method for anatomically indexing a subject, comprising:

receiving, by an image processor, image scan data representing a volume of a subject, the image scan data being comprised of a plurality of image slices of the subject and including at least a portion of a vertebral column of the subject, the vertebral column having a vertebral canal and comprised of a plurality of vertebral bodies;

identifying, by the image processor, the vertebral canal of the vertebral column of the subject in the image scan data;

extracting, by the image processor, image features from the image scan data;

determining, by the image processor, a plurality of markers for the vertebral column from the extracted image features, each marker in the plurality of markers is indicative of a different vertebral body of the vertebral column and includes an identifier for the vertebral body and coordinates for the given marker in the image scan data, where the coordinates are defined in a first coordinate system associated with the image scan data such that the coordinates for the plurality of markers define at least one origin of a vertebral level coordinate system and the first coordinate system associated with the image scan data differs from the vertebral level coordinate system; and storing, by the image processor, each marker in the plurality of markers along with its coordinates in a database, wherein the image processor is embodied as computer executable instructions executed by a computer processor.

2. The computer-implemented method of claim 1, further comprising:

determining a location of an anatomical component of the subject in the image scan, where the anatomical component differs from the vertebral column and the location being defined as a vertebral level coordinate in the vertebral level coordinate system;

determining a measure corresponding to the anatomical component of the subject;

associating the measure with the vertebral level coordinate of the anatomical component; and storing the measure in the database.

3. The method of claim 1 further comprises capturing the image scan data using computed tomography.

4. The method of claim 3 further comprises obtaining an identifier of the image scan data; and relating the plurality of markers to the identifier of the image scan data.

5. The method of claim 1 where a given marker is located at an intersection point between a given vertebral body and the vertebral canal.

6. The method of claim 1 wherein a given marker is located at intersection of a plane through a disc immediately below a corresponding vertebral body and a center of the vertebral canal in the corresponding vertebral body.

7. The method of claim 5 wherein determining the plurality of markers further comprises determining an anterior marker and a posterior marker for each intervertebral disc of the vertebral column captured in the image scan, where the anterior marker is positioned at an anterior position of a given intervertebral disc and the posterior marker is positioned at a posterior position of the given intervertebral disc.

8. The method of claim 1, further comprising:

locating at least one section of skin of the subject in the image scan;

generating at least one skin marker corresponding to the at least one section of the skin; and storing the skin marker in the database, the at least one skin marker defining a body surface coordinate system.

9. The method of claim 1 further comprises searching for a kidney of the subject using one or more of the plurality of markers; segmenting image data containing the kidney form the image scan data and computing one of a volume or surface area of the kidney from the segmented image data.

10. A computer-implemented method for anatomically indexing a subject, comprising:

retrieving, by an image processor, a plurality of markers for a vertebral column, the vertebral column having a vertebral canal and comprised of a plurality of vertebral bodies, each marker in the plurality of markers is indicative of a different vertebral body of the vertebral column and includes an identifier for the vertebral body and coordinates for the given marker in the image scan data, where the coordinates are defined in a first coordinate system associated with the image scan data, such that the coordinates of the plurality of markers define at least one axis of a vertebral level coordinate system and the first coordinate system associated with the image scan data differs from the vertebral level coordinate system;

determining, by the image processor, location of an anatomical component of the subject from image scan data representing a volume of the subject, where the anatomical component differs from the vertebral column and the image scan data being comprised of a plurality of image slices of the subject and including at least a portion of a vertebral column of the subject;

determining, by the image processor, a measure for the anatomical component;

expressing the location of the anatomical component in relation to the vertebral level coordinate system; and storing, by the image processor, the measure for the anatomical component along with the location of the anatomical component in a database, wherein the image processor is embodied as computer executable instructions executed by a computer processor.

11. The method of claim 10 further comprises receiving, by the image processor, the image scan data representing a volume of a subject;

identifying, by the image processor, the vertebral canal of the vertebral column of the subject in the image scan data; and determining, by the image processor, a plurality of markers for the vertebral column.

12. The method of claim 10 further comprises capturing the image scan data using computed tomography.

13. A computer-implemented method for anatomically indexing a subject, comprising:

receiving input image data representing a volume of a subject, the input image data including at least a portion of a vertebral column of the subject;

identifying the vertebral column of the subject in the input image data;

determining one or more markers for the vertebral column, where each of the markers is indicative of the location of vertebral column and the location is defined as coordinates in coordinate system associated with the image data;

defining a vertebral coordinate system using the markers, where the coordinates for one or more markers define at least one origin of the vertebral coordinate system and the vertebral coordinate system differs from the coordinate system associated with the image data;
locating another anatomical component in the subject using at least one of the markers for the vertebral column, the anatomical component differs from the vertebral column and being selected from the group comprised of an organ, a muscle and a bone;
determining a measure for the anatomical component;
determining location of the anatomical component in relation to the vertebral coordinate system; and
storing the measure for the anatomical component, along with the location of the anatomical component, in a database.

14. The method of claim 13 further comprises capturing the image data using computed tomography.

15. The method of claim 13 wherein determining one or more markers for the vertebral column further comprises determining location of a spinal canal in the vertebral column and determining a spinal marker for each vertebra of the vertebral column captured in the image data, where the spinal marker is positioned at a center of the spinal canal.

16. The method of claim 15 wherein determining one or more markers for the vertebral column further comprises determining an anterior marker and a posterior marker for each intervertebral disc of the vertebral column captured in the image data, where the anterior marker is positioned at an anterior position of a given intervertebral disc and the posterior marker is positioned at a posterior marker of the given intervertebral disc.

17. The method of claim 13 wherein locating another anatomical component further comprises searching for a kidney of the subject using the markers for the vertebral column, segmenting image data containing the kidney from the input image data and computing at least one of a volume or a surface area of the kidney from the segmented image data.

18. The method of claim 13 further comprises locating a psoas muscle in the subject and measuring a cross section of the psoas muscle at a given vertebra of the vertebral column.

19. The method of claim 1 further comprises determining a marker for the anatomical component and storing the markers for the anatomical component in the database, where the marker is indicative of the location of the anatomical component and defined in the common coordinate system.

* * * * *